United States Patent [19]

Porter

[11] Patent Number: 5,571,129
[45] Date of Patent: Nov. 5, 1996

[54] SURGICAL CUTTING INSTRUMENT WITH IMPROVED CLEANING CAPABILITY AND EASE OF USE

[75] Inventor: David E. Porter, Center Sandwich, N.H.

[73] Assignee: Portlyn Corporation, Moultonboro, N.H.

[21] Appl. No.: 441,381

[22] Filed: May 15, 1995

[51] Int. Cl.$^6$ ..................................... A61B 17/32
[52] U.S. Cl. ............................ 606/170; 604/95; 604/170; 128/751; 128/750
[58] Field of Search ................... 128/751, 4, 5, 128/6, 7, 8, 749, 750, 752; 264/173; 604/95, 170, 171; 606/170

[56] References Cited

U.S. PATENT DOCUMENTS

| | | | |
|---|---|---|---|
| 4,817,630 | 4/1989 | Schintgen et al. | 128/751 |
| 5,061,238 | 10/1991 | Shuler | 604/22 |
| 5,075,062 | 12/1991 | Karpiel | 264/173 |
| 5,250,073 | 10/1993 | Cottone, Jr. | 606/206 |
| 5,320,635 | 6/1994 | Smith | 606/180 |
| 5,322,505 | 6/1994 | Krause et al. | 604/24 |
| 5,324,301 | 6/1994 | Drucker | 606/180 |

OTHER PUBLICATIONS

"DynaBite, Biopsy Forceps", Portlyn Medical Products: Copyright 1993.
"A Total Manufacturing Capability Dedicated To Medical Products And Components" Portlyn Medical Products: Copyright 1993.

*Primary Examiner*—Michael Powell Buiz
*Assistant Examiner*—Kevin Truong
*Attorney, Agent, or Firm*—Hayes, Soloway, Hennessey, Grossman & Hage, P.C.

[57] ABSTRACT

A surgical cutting instrument comprising an elongated flexible hollow-body tube having a lumen extending therethrough, and having a proximal end and distal end. A cutting, grasping or manipulating mechanism is coupled to the distal end of the body portion. Control wire means having proximal and distal ends, extend through the lumen in the body portion, and are coupled to the cutting grasping or manipulating mechanism. The control wire means contains on its surface a polymeric film resin to reduce friction between the control wire and inner surface of the flexible hollow body tube, and/or to seal the control wire within the flexible hollow body tube.

5 Claims, 2 Drawing Sheets

SURGICAL CUTTING INSTRUMENT WITH IMPROVED CLEANING CAPABILITY AND EASE OF USE

BACKGROUND OF THE INVENTION

1. Field of the Invention

The present invention pertains to improvements in surgical cutting instruments. The invention has particular utility in connection with surgical cutting instruments of the type described in copending application Ser. No. 08/422,049 now pending assigned to the coon assignee, and will be described in connection with such utility, although other utilities are contemplated.

2. Background

The use of elongated surgical cutting instruments has become well accepted in performing closed surgery, such as orthoscopic or, more generally, endoscopic surgery. As described in U.S. Pat. No. 5,061,238, in closed surgery, access to the surgical site is gained via one or more portals, and instruments used in the surgical procedure must be elongated to permit the distal ends of the instruments to reach a desired location in a patient. Surgical cutting instruments for use in closed surgery conventionally have an elongated outer tubular member terminating at a distal end having an opening in a side wall, the end wall, or both, to form a cutting port or window end and an elongated inner tubular member concentrically disposed in the outer tubular member and having a distal end disposed adjacent the opening in the distal end of the outer tubular member. The distal end of the inner tubular member has a surface or edge for engaging tissue via the opening in the distal end of the outer tubular member and in many cases cooperates with the opening to shear and cut tissue. The '238 patent goes on to disclose an elongated bearing structure for a surgical cutting instrument having elongated inner and outer tubular members which are said to prevent cocking or skewing of the inner member relative to the outer member without creating galling and possible seizure during operation of the surgical cutting instrument.

In U.S. Pat. No. 5,250,073, there is described a torqueable and formable biopsy forceps. The biopsy forceps are said to provide improved torqueable and formable characteristics. The device includes a handle and core wire connected at its proximal end to the handle and connected at its distal end to a forceps assembly. The control wire displacing device carried by the handle serves to displace the core wire for moving the core wire between a forceps open position and a forceps closed position. The core wire includes at least three elongated portions, including a proximal portion having a proximal end secured to the wire displacing means, a distal portion having a distal end secured to the forceps assembly and an intermediate portion located between the proximal and distal portions. The proximal portion is said to be of greater length than the intermediate or distal portions and of greater diameter than the intermediate portion which, in turn, is said to be of greater diameter than the distal portion.

In U.S. Pat. No. 5,324,301, there is described a surgical instrument comprising inner and outer tubular members with a coating of tin-nickel alloy on the outer surface of the inner tubular member and/or the inner surface of the outer tubular member to provide an elongated bearing surface between the tubular members.

In U.S. Pat. No. 5,322,505, there is described a surgical instrument that includes a rigid outer member within which is disposed a hollow inner member having rigid proximal and distal ends and a region disposed between the rigid proximal and distal ends that is relieved to render such region flexible.

With regards to the above, although various prior art devices have been manufactured, as noted, to improve the performance of surgical instruments for closed surgery procedures, one long-standing problem has emerged which is the tendency of such surgical cutting instruments to rotate in the direction corresponding to the wire wrapping on the surface of the outer jacket. That is, the surgical cutting instruments of the prior art generally have disposed on the outer jacket a wire-wrap with a constant and continuous right or left-hand wrap configuration. As a consequence, upon activation of the control wire displacement means which runs through the inner regions of the outer tubular member, the surgical cutting instrument tends to rotate or torque in the direction of the wrap. Moreover, there is a measured reduction in the force transmitted to the distal end cutting jaws.

Accordingly, in my copending application Ser. No. 08/422,049, it was a primary object of the invention to overcome the various problems and disadvantages associated with surgical cutting instruments of the prior art both which tend to displace from a target location, and sacrifice cutting strength, in a closed surgical procedure. In particular, it was disclosed that one could achieve this objective by providing a surgical cutting instrument which contained an anti-torque outer jacket, which eliminates torque distortion and reduces the loss in force delivered to the distal cutting means.

With respect to the development of the anti-torque outer jacket, as noted above, it became apparent that many of the devices of the prior art, including those devices that did not contain such anti-torque outer jackets, were problematic in their operation, from the point of view of their ease of use, sterilizability and/or ability to be cleaned. That is, the inner control wire of the device, which connected to the cutting means, and which was multi-stranded itself, would necessarily create a small but nevertheless significant region for body fluids or tissue to become fixed after use.

In addition, the control wire means of the prior art would necessarily contact the inner surface of the hollow-body lumen, and when displaced, create some metal-to-metal frictional resistance with said surface of the lumen.

Accordingly, it has become an object of this invention to overcome the above disadvantages associated with the prior art, and provide a control wire means, surrounded with a coating, such that the coating reduces friction as between the control wire means and outer lumen, and in addition, provides a seal as against the uptake of body fluids or small tissue.

In particular, it is an object of this invention to provide a plastic film tubing surrounding the inner control wire means of a surgical cutting instrument, characterized in that the tubing collectively improves the ease of use of the instrument, minimizes contamination, and renders more efficient the reuse, cleaning and/or sterilization procedures.

SUMMARY OF THE INVENTION

The present invention provides a surgical instrument comprising an elongated flexible hollow-body tube having a lumen extending therethrough, and having a proximal end and distal end. A means for cutting, grasping or manipulating tissue is coupled to the distal end of the body portion.

Control wire means having proximal and distal ends, extend through the lumen in the body portion and are coupled to its distal end to the cutting, grasping or manipulating means. The control wire means contains on its surface a means to reduce friction as between the control wire and inner surface of the flexible hollow body tube, and/or to seal the control wire within the flexible hollow body tube.

BRIEF DESCRIPTION OF THE DRAWINGS

Further objects and advantages of the present invention will become clear from the following detailed description taken with the accompanying drawings, wherein like numbers depict like parts and wherein.

DESCRIPTION OF THE PREFERRED EMBODIMENT

Figure 1:
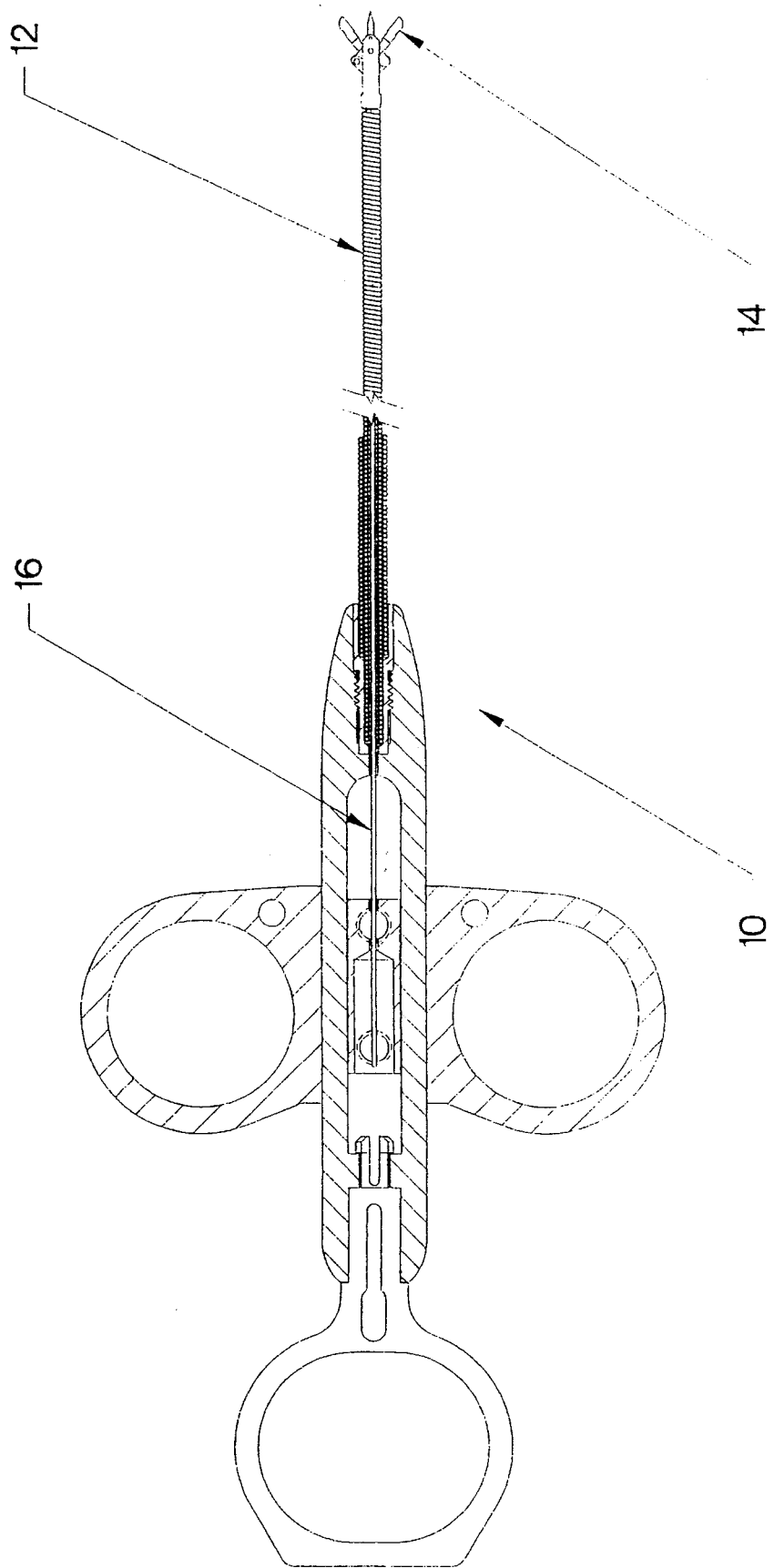
FIG. 1 is a side elevation of one embodiment of surgical cutting instrument according to the present invention.

With reference to FIG. 1 a surgical cutting instrument 10 shown comprising an elongated, flexible, hollow-body tube 12 having a lumen extending therethrough, and having a proximal end and distal end, a means for cutting coupled to the distal end of said body portion 14, a control wire means 16 having proximal and distal ends extending through the lumen in said body portion and coupled at said distal end to said cutting means.

Figure 2:
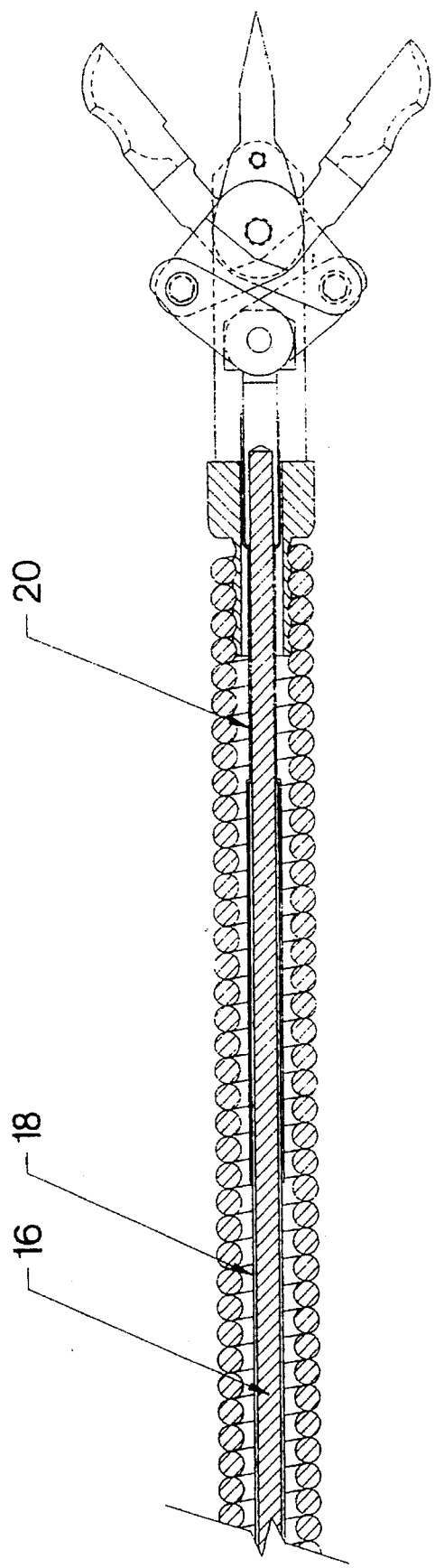
FIG. 2 is an enlarged side elevation, partially broken away, of the distal end of the surgical cutting instrument of FIG. 1.

As noted, FIG. 2 is an enlarged side elevation, partially broken away, of the distal end of the surgical cutting instrument of FIG. 1. As can be seen in FIG. 2, the control wire means 16 contains on its surface a means 18 to reduce friction as between the control wire and inner surface of the hollow tube 12. In a preferred embodiment means 18 comprises a polymeric film coating, in particular, a fluoropolymer film coating, which is preferably extruded over the control wire means to provide lubricity to said control wire when the device is operated as between open and closed position to either cut, grasp or manipulate body tissue. However, it can be appreciated that other methods may be employed to coat the control wire means, such as dip-coating in a solvent containing the polymer resin to be applied. In any event, those fluoropolymers which are suitable for melt application include the family of polytetrafluoroethylene resins, such as ethylene-tetrafluoroethylene, perfluoroaltoxytetrafluoroethylene, chlorotrifluoroethylene and other fluoropolymers, which can be applied to the control wire means by the aforementioned techniques. Moreover, those skilled in the art will appreciate that non-fluoropolymer coatings can operate in the context of this invention, e.g. the family of olefin polymers and condensation type polymers, as well.

In addition, said coating advantageously minimizes contamination when the instrument is placed in body fluid, by preventing body fluid or for that matter body particulate from becoming lodged in the small inner region as between the control wire means, and the outer jacket, or between the filaments which may comprise the control wire means itself.

As also shown in FIG. 2, in the situation where the end of the control wire means must be affixed to a cutting instrument by a high temperature brazing step, the distal end of the control wire is first stripped away, to allow for the brazing operation. This is followed by placing a heat shrinkable tubing 20 over the stripped away distal end. In this manner, the control wire means is effectively sealed end-to-end to provide the advantageous features of the invention previously discussed.

Finally, still other variations, modifications and changes in detail may be made without departing from the spirit and scope of the invention. It is therefore intended that the subject matter discussed above, and shown in the accompanying drawings be interpreted as being illustrative and not in a limiting sense.

I claim:

1. A surgical cutting instrument comprising
    an elongated flexible hollow-body tube having a lumen extending therethrough, and having a proximal end and distal end,
    a means for cutting, grasping or manipulating tissue coupled to the distal end of said body portion,
    control wire means having proximal and distal ends, extending through the lumen in said body portion and coupled to its distal end to said cutting means,
    characterized in that the control wire means contains on its surface a means surrounding and sealing the control wire means and extending from the distal end, and sealing the control wire within the flexible hollow body tube therein, providing a seal as against the uptake of body fluids or small tissue.

2. The surgical cutting instrument of claim 1, wherein the means surrounding the control wire comprises a polymeric film resin.

3. The surgical cutting instrument of claim 2, wherein the polymer film resin is a fluoropolymer.

4. The surgical instrument of claim 3, wherein the fluoropolymer is polytetrafluoroethylene or ethylenetetrafluoroethylene film.

5. The surgical cutting instrument of claim 1, wherein the means surrounding the control wire means extends end-to-end.

* * * * *